United States Patent [19]

Nakanishi

[11] Patent Number: 4,458,070

[45] Date of Patent: Jul. 3, 1984

[54] PROCESS FOR THE MANUFACTURE OF CRYSTALLINE SODIUM CEFOPERAZONE

[75] Inventor: Susumu Nakanishi, Itayamaazani, Japan

[73] Assignee: Pfizer Inc., New York, N.Y.

[21] Appl. No.: 399,400

[22] Filed: Jul. 19, 1982

[51] Int. Cl.$^3$ ................ C07D 501/36; A61K 31/545
[52] U.S. Cl. ...................................... 544/27; 424/246
[58] Field of Search ...................... 544/28, 27, 21, 22; 424/246

[56] References Cited

U.S. PATENT DOCUMENTS 4,087,424  5/1978  Saikawa et al. ...................... 544/28

FOREIGN PATENT DOCUMENTS 1508071  4/1978  United Kingdom ................. 544/21

Primary Examiner—Nicholas S. Rizzo
Attorney, Agent, or Firm—Charles J. Knuth; Albert E. Frost; James M. McManus

[57]  ABSTRACT

Crystalline sodium cefoperazone and a process for the preparation thereof comprising the combining of an aqueous acetone solution of sodium cefoperazone with a solution of acetone-methylene chloride.

5 Claims, No Drawings

PROCESS FOR THE MANUFACTURE OF CRYSTALLINE SODIUM CEFOPERAZONE

FIELD OF THE INVENTION

This invention relates to a novel, convenient and economic process for producing sodium cefoperazone. More particularly, it relates to the production of crystalline sodium cefoperazone essentially free of residual organic solvents.

DESCRIPTION OF THE ART

Cefoperazone is a broad spectrum beta-lactam antibiotic which is usually administered parenterally as the sodium salt, which is provided by the available procedures (British Patent Specification No. 1,508,071) as an amorphous solid.

Amorphous compounds are, in general, less desirable than is a crystalline form thereof from the standpoint of preparation, storage and use.

A crystalline compound is considerably more stable than an amorphous form of the compound, and resists decomposing and discoloration. For pharmaceutical use, it is much easier to make up a particular dosage form using a crystalline compound as opposed to an amorphous form thereof. Finally, amorphous forms of a compound are frequently more hygroscopic than the crystalline form.

SUMMARY OF THE INVNENTION

It has now been discovered that a relatively simple, inexpensive process can be used to obtain crystalline sodium cefoperazone which is essentially free of residual organic solvents which comprises the steps of combining an aqueous acetone solution containing from about 3 to 30 percent by weight of sodium cefoperazone with about a four-fold volume of acetonemethylene chloride (95:5, v/v) at a temperature of about 5°-40° C.; and separating and drying the resulting crystalline sodium cefoperazone.

The process utilizes readily available equipment and is characterized by ease of manipulation, overall economy and high quality of the crystalline compound. The stable crystalline sodium cefoperazone of the present invention is useful in the same dosage forms and amounts for the same purposes as are the amorphous prior art products, but does not share the abovementioned shortcomings of the amorphous product.

Also part of the present invention is crystalline sodium cefoperazone.

DETAILED DESCRIPTION OF THE INVENTION

The novel process of this invention can be used to prepare crystalline sodium cefoperazone from an aqueous acetone solution containing from about 3 to 30 percent (w/v) sodium cefoperazone, with a preferred content of 5 to 15 percent (w/v).

The aforementioned aqueous acetone solution of sodium cefoperazone is conveniently prepared in situ by treating an acetone solution or suspensions containing from about 5 to 35 percent (w/v) of cefoperzone free acid with an aqueous solution containing about one equivalent of a basic compound such as sodium hydroxide, sodium bicarbonate or sodium carbonate. As one skilled in the art is aware, many other sources of sodium bases can be employed in order to generate sodium cefoperazone in situ such as sodium ethyl hexanoate.

The resulting aqueous acetone solution of sodium cefoperazone is treated with about a four-fold volume (v/v) of a solution of acetone-methylene chloride (95:5, v/v). A smaller volume of this solution can be employed without departing from the spirit of the invention, but the yield of recovered crystalline sodium cefoperazone will be decreased. The temperature for the combining of these solutions is about 5°-40° C., with a preferred temperature range of 15°-23° C.

Following the precipitation of the crystalline sodium cefoperazone the mixture is allowed to stir for about 1 hour, followed by filtration and drying.

The drying can be carried out at room temperature under vacuum, or it can be done at elevated temperatures under vacuum. The preferred temperature for drying is about 42° C. under a vacuum of 1.5 mm Hg. Under these preferred conditions the crystalline sodium cefoperazone is dry in about 15–16 hours.

Frequently, when organic solvents are employed in the formation of crystalline salts of organic compounds, large amounts of unwanted organic solvents are trapped in the crystal structure of the salt and render them unfit for human use or require extraordinary drying conditions to reduce the amount of organic solvent to a range acceptable for human use. The process of the present invention provides crystalline sodium cefoperazone which is essentially free of residual organic solvents without resort to stringent drying conditions.

As previously mentioned, sodium cefoperazone is a broad spectrum antibiotic useful in treating bacterial infections in humans. The use of this compound for this purpose is described in the art including British Patent Specification No. 1,508,071 and U.S. Patent No. 4,087,424.

The following examples are provided solely for the purpose of further illustration.

EXAMPLE 1

To a slurry of 10 g. of cefoperazone free acid in 30 ml. of acetone was added 1.23 g. of sodium bicarbonate in 11.3 ml. over a period of 30 minutes while the temperature was maintained at about 4°-6° C. To the resulting solution, having a pH of less than 6.5, was added dropwise with stirring 37 ml. of a solution of acetone-methylene chloride (95:5, v/v) while the temperature is maintained at about 15°-20° C., and the mixture allowed to stir for 1 hour. Methylene chloride (66 ml.) was added dropwise over a period of 17 minutes and the suspension, after stirring for 1 hour, was filtered, washed with methylene chloride, and dried at 42° C. (1.5 mm Hg.) for 15 hours, 9.3 g. (95% yield).

The product, sodium cefoperazone, contained 0.003% residual acetone, 0.12% methylene chloride and 1.9% water.

EXAMPLE 2

To a suspension of 3.3 g. of cefoperazone free acid in 30 ml. of acetone cooled to 4°-8° C. is added 196 mg. of sodium hydroxide in 10 ml. of water over a period of 10 minutes with cooling to maintain the temperature at 4°-8° C. To the resulting solution is added 40 ml. of acetone-methylene (95:5, v/v) dropwise with stirring over a period of 20 minutes, the temperature being maintained at about 5°-15° C. After the resulting slurry has been stirred for 1 hour, an additional 120 ml. of acetone-methylene chloride (95:5, v/v) is added at 5°–15° C. and the stirring continued for 1 one hour. Methylene chloride (50 ml.) is added over a period of 15 minutes, and the slurry is allowed to stir an additional hour. The suspension is filtered and the desired product washed with methylene chloride and dried at about 42° C. (1.5 mm Hg.) for 16 hours.

EXAMPLE 3

To a suspension of 14.2 g. of cefoperazone in 60 ml. of acetone is added 1.1 g. of sodium carbonate in 22 ml. of water over a period of 45 minutes while the temperature is maintained at 4°–6° C. To the resulting mixture is added dropwise with stirring 80 ml. of acetone-methylene chloride (95:5, v/v) while the temperature is maintained at 35°–40° C. After stirring for 2 hours an additional 280 ml. of acetone-methylene chloride (95:5, v/v) is added and the stirring continued for 2 hours. The suspension is filtered and the solids washed with methylene chloride. The crystalline sodium cefoperazone is dried at 42° C. (1.5 mm Hg.) for 18 hours.

I claim:

1. A process for the manufacture of crystalline sodium cefoperazone essentially free of residual organic solvents which comprises the steps of combining an aqueous acetone solution containing from about 3 to 30 percent (w/v) of sodium cefoperazone with about a four-fold volume (v/v) of a solution of acetone-methylene chloride (95:5, v/v) at a temperature of about 5°–40° C.; and separating and drying the resulting crystalline sodium cefoperazone.

2. The process of claim 1 wherein said aqueous acetone solution containing sodium cefoperazone is formed in situ by combining an acetone solution or suspension containing from about 5 to 35 percent (w/v) of cefoperazone free acid with an aqueous solution containing about one equivalent of a base selected from the group consisting of sodium hydroxide, sodium carbonate and sodium bicarbonate.

3. The process of claim 1 wherein said aqueous acetone solution contains from about 5 to 15 percent (w/v) of sodium cefoperazone, and the combining of said solution with said solution of acetone-methylene chloride is carried out at about 15°–23° C.

4. The process of claim 1 wherein said separating is by filtration and said drying is under vacuum (1.5 mm Hg.) at about 42° C.

5. Crystalline sodium cefoperazone.

* * * * *